(12) United States Patent
Tanaka et al.

(10) Patent No.: US 7,634,362 B2
(45) Date of Patent: Dec. 15, 2009

(54) METHOD FOR JUDGING FEATURE OF MALIGNANT TUMOR

(75) Inventors: Satoshi Tanaka, Kobe (JP); Hideki Ishihara, Miki (JP)

(73) Assignee: Sysmex Corporation, Hyogo (JP)

( * ) Notice: Subject to any disclaimer, the term of this patent is extended or adjusted under 35 U.S.C. 154(b) by 242 days.

(21) Appl. No.: 11/496,397

(22) Filed: Aug. 1, 2006

(65) Prior Publication Data

US 2007/0141651 A1  Jun. 21, 2007

(30) Foreign Application Priority Data

Aug. 1, 2005  (JP) ............... 2005-223039

(51) Int. Cl.
  A61K 31/00   (2006.01)
  A61K 31/337  (2006.01)
  A61K 33/24   (2006.01)
  A61P 35/00   (2006.01)
  G01N 33/53   (2006.01)

(52) U.S. Cl. .................. 702/19; 435/7.23; 530/350

(58) Field of Classification Search ............... None
See application file for complete search history.

(56) References Cited

U.S. PATENT DOCUMENTS

| | | | |
|---|---|---|---|
| 2003/0050470 A1* | 3/2003 | An et al. ................. | 536/24.3 |
| 2004/0018525 A1 | 1/2004 | Wirtz et al. | |
| 2004/0229294 A1 | 11/2004 | Chan-Hui et al. | |
| 2005/0079518 A1* | 4/2005 | Baker et al. ............... | 435/6 |
| 2005/0131057 A1 | 6/2005 | Ueno et al. | |
| 2007/0134669 A1* | 6/2007 | Verjat ...................... | 435/6 |
| 2008/0153098 A1* | 6/2008 | Rimm et al. ............... | 435/6 |

FOREIGN PATENT DOCUMENTS

| | | | |
|---|---|---|---|
| EP | 1 233 060 A2 | 8/2002 | |
| EP | 1 512 755 A2 | 3/2005 | |
| EP | 1 600 513 A1 | 11/2005 | |
| GB | 2 334 578 A | 8/1999 | |
| WO | WO 00/47998 | 8/2000 | |
| WO | WO 02/096867 | 12/2002 | |
| WO | 2004/076686 | * | 9/2004 |

OTHER PUBLICATIONS

Ishihara et al. "A new cancer diagnostic system based on a CDK profiling technology" Biochimica et Biophysica Acta, vol. 1741, No. 3, Jun. 20, 2005, pp. 226-233, XP002402956.

Ross et al, "Molecular Biology/Biochemistry 13 HER-2/NEU Oncogene Amplification and P34CDC2 Cyclin Dependent Kinase Overexpression Predict Recurrence in Protate Cancer", Proceedings for the Annual Meeting of the American Association for Cancer Research, New York, NY, US, vol. 38, Mar. 1997, p. 277, 1, XP002926940, Abstract.

Heikki Joensuu et al., "Amplification of *erb*B2 and erbB2 Expression Are Superior to Estrogen Receptor Status As Risk Factors for Distant Recurrence in pT1N0M0 Breast Cancer: A Nationwide.Population-based Study", Clinical Cancer Research, Mar. 2003, 923-930, vol. 9.

* cited by examiner

*Primary Examiner*—Michael Borin
(74) *Attorney, Agent, or Firm*—Sughrue Mion, PLLC (57) ABSTRACT

A method for judging feature of malignant tumor is described herein. The method comprises obtaining step, first comparing step, second comparing step, and judging step. The obtaining step comprises obtaining a first parameter based on activity and expression level of a first CDK contained in a tumor cell of the malignant tumor, a second parameter based on activity and expression level of a second CDK contained in the tumor cell, a third parameter based on the first parameter and the second parameter, and a fourth parameter based on expression level of a growth factor receptor in the tumor cell. The first comparing step comprises comparing a first threshold value with the third parameter. The second comparing step comprises comparing a second threshold value with the fourth parameter. The judging step comprises judging the feature based on the comparison results of the first comparing step and the second comparing step. Also described is a computer program or program product executing the steps of the method.

8 Claims, 5 Drawing Sheets

METHOD FOR JUDGING FEATURE OF MALIGNANT TUMOR

TECHNICAL FIELD

The present invention relates to a method for judging a feature of a malignant tumor based on an analysis result obtained through analysis of protein of a tumor cell collected from a patient having the malignant tumor.

BACKGROUND

It is conventionally known that a feature of a malignant tumor can be judged based on a measured expression level of HER2 of a malignant tumor cell. In Joensuu H., et al. (Clinical Cancer Research, vol. 9, 2003, 923-930), the expression level of the HER2 is used to predict prognosis of early breast cancer. The HER2 is a growth factor receptor having a tyrosine kinase activity, and it is generally interpreted that the malignant tumor in which HER2 is expressed at a high level involves a high risk of recurrence, while the risk of recurrence is low in the malignant tumor in which HER2 is expressed at a low level. However, even the malignant tumor undergoing the low HER2 expression level still involves some risk of recurrence, and the prognosis of the malignant tumor based on the expression level of the HER2 has failed to be very accurate.

SUMMARY

The scope of the present invention is defined solely by the appended claims, and is not affected to any degree by the statements within this summary.

A main object of the present invention is to provide a method for judging a feature of a malignant tumor with a high accuracy based on an analysis result obtained through analysis of molecules expressed in a tumor cell collected from a patient having the malignant tumor.

A first aspect of the present invention relates to method for judging feature of malignant tumor, comprising steps of:

obtaining a first parameter based on activity and expression level of a first cyclin dependent kinase (CDK) contained in a tumor cell of the malignant tumor, a second parameter based on activity and expression level of a second CDK contained in the tumor cell, a third parameter based on the first parameter and the second parameter, and a fourth parameter based on expression level of a growth factor receptor in the tumor cell;

first comparing a first threshold value with the third parameter;

second comparing a second threshold value with the fourth parameter; and judging the feature based on the comparison results of the first comparing step and the second comparing step.

DETAILED DESCRIPTION OF THE PREFERRED EMBODIMENTS

According to the present embodiment, the method capable of accurately judging the feature of the malignant tumor based on the analysis results of the cyclin dependent kinases (CDKs) and the growth factor receptor expressed in the tumor cell collected from the patient having the malignant tumor can be provided.

According to the method of the present embodiment, the first parameter, the second parameter, the third parameter and the fourth parameter are obtained as an initial step.

The first parameter is based on the activity value and the expression level of the first cyclin dependent kinase (first CDK) contained in the tumor cell collected from the patient having the malignant tumor.

The second parameter is based on the activity value and the expression level of the second cyclin dependent kinase (second CDK) contained in the tumor cell.

The third parameter is calculated from the first parameter and the second parameter.

The fourth parameter is based on the expression level of the growth factor receptor contained in the tumor cell.

The method according to the present embodiment includes the first comparing step for comparing the third parameter to the first threshold value, the second comparing step for comparing the fourth parameter to the second threshold value, and the step for judging the feature of the malignant tumor based on the results of these comparing steps.

Examples of the malignant tumor to which the foregoing judging method is applied include a malignant tumor derived from a hematopoietic organ, carcinoma derived from an epithelial cell, sarcoma and the like. Examples of the malignant tumor derived from the hematopoietic organ include leukemia, malignant lymphoma and the like. Examples of the carcinoma include breast cancer, stomach cancer, large intestine cancer, esophagus cancer, prostate cancer and the like. Examples of the sarcoma include osteogenic sarcoma, sarcoma developed in soft parts and the like.

The tumor cell used in the method is preferably a malignant tumor cell in "stage IIB" in stage classification.

The stage classification is a type of classification in which a malignancy of the malignant tumor is shown, wherein the malignant tumor is classified into, from lower levels of the malignancy, stages I, IIA, IIB, IIIA, IIIB and IV. The stage classification is based on TNM classification. The TNM classification is a stage classification of the malignant tumor according to the Unio Internationalis Contra Cancrum (UICC, International Union Against Cancer). "T" denotes a size of a primary tumor and ranges from T0 (primary lesion cannot be confirmed) through T4 (tumor is exposed out of body). "N" denotes a degree of invasion into lymphonodus in vicinity and ranges from N0 (no metastasis into lymphonodus) through N3 (metastasis into lymphonodus in vicinity of a median part of a body (lymphonodus in vicinity of breast bone) is suspected). "M" denotes presence or absence of remote metastasis and ranges from M0 (no remote metastasis) through M1 (remote metastasis is confirmed).

The malignant tumor in the stage IIB indicates the malignant tumor in "T2, N1, M0" or "T3, N0, M0" in the TNM classification.

Examples of the feature of the malignant judged in the foregoing judging method include a proliferation potency and a risk of recurrence (likelihood of metastasis) of the tumor cell, and the like. This judging method is preferably used particularly for judging the risk of recurrence. The recurrence is diagnosed when the malignant tumor recurs in a body part from which the tumor is extirpated after a predetermined length of time has passed since the extirpation and when the tumor cell, which is separated from the primary tumor, is transported into a remote tissue to independently proliferate therein. The possibility of the recurrence depends on the proliferation potency, survival potency and migratory aptitude of the tumor cell, and the like.

The CDK is a collective term for enzymes activated through binding of protein called cyclin and functions in a particular stage of a cell cycle depending on a type thereof. The types of the CDK are CDK1, CDK2, CDK3, CDK4, CDK5, CDK6, CDK7, and the like. In the present embodiment, at least two types of CDKs (first CDK and second CDK) are used, and CDK1 and CDK2 are preferably used in combination. More specifically, the first CDK is preferably used as the CDK1, and the second CDK as the CDK2, or the first CDK is preferably used as the CDK2, and the second CDK as the CDK1.

The first parameter is obtained from the activation value and the expression level of the first CDK, while the second parameter is obtained from the activation value and the expression level of the second CDK. As these parameters, one of the activation value and the expression level may be solely used, or a value calculated through addition, subtraction, multiplication and division of the activation value and the expression level may be used, and a ratio of the activation value and the expression level is preferably used. As the ratio of the activation value and the expression level, a value obtained by dividing the activation value by the expression level (specific activity), a value obtained by dividing the expression level by the activation value (inverse number of specific activity), or the like, can be used.

The third parameter is obtained based on the first parameter and the second parameter. The third parameter can employ a value calculated through addition, subtraction, multiplication and division of the first parameter and the second parameter. A ratio of the first parameter and the second parameter is preferably used as the third parameter. The ratio of the first parameter and the second parameter can adopt a value obtained by dividing the first parameter by the second parameter, a value obtained by dividing the second parameter by the first parameter, or the like.

The fourth parameter is obtained based on the expression level of the growth factor receptor included in the tumor cell. The expression level may be solely used, or a value calculated from addition, subtraction, multiplication and division of the expression level and the activation value may be used as the fourth parameter. The expression level is preferably, solely used.

The growth factor receptor is a receptor in which the growth factor serves as a ligand and plays an important role in controlling the proliferation and differentiation of the cell. In the present embodiment, protein which belongs to a HER (Human Epidermal Growth Factor Receptor) family is preferably used as the growth factor receptor. HER1, HER2, HER3 and HER4 are currently known as the protein which belongs to the HER family, and the HER2 is particularly preferably used.

In the first comparing step, the third parameter is compared to the corresponding threshold value (hereinafter, referred to as first threshold value).

The first threshold value is appropriately set depending on what feature of the tumor cell is to be judged. For example, in the case of judging the recurrence risk of breast cancer, the first threshold value can be set as a value capable of dividing a group of breast cancer patients in to a high-value group and a low value group in a certain proportion.

In the case of breast cancer whose recurrence ratio in five years after the extirpative surgery is approximately 30%, the proportion of the separation of the high-value group is preferably at least 30% of the group of patients, for example. The proportion higher than 30% is more preferably set to the high-value group so that the recurrence does not occur in the patients divided into the low-value group. More specifically, the first threshold value can adopt such values that the proportion of the high-value group: low-value group in the group of patients results in 30:70, preferably 40:60, or more preferably 50:50 (median) or 60:40. It is unnecessary to so strictly set the proportion of the separation because such values that can divide the group of patients as exactly 50:50 or 60:40 may not possibly exist. For example, when the number of the patients constituting the group of patients is 99, there does not exist such a value that can divide the group of patients as 50:50, in which case, the proportion of the separation may be set to 50:49.

Depending on the tumor cell, the first parameter or the second parameter, or the both parameters may have a very small value or a very large value, and the third parameter thereby may show a value significantly different to the first threshold value. In such a case, it is preferable to set not only the first threshold value but also threshold values for the first and second parameters. More specifically, it is preferable that the first parameter be compared to a threshold value corresponding thereto, the second parameter be compared to a threshold value corresponding thereto, and the third parameter be compared to the first threshold value in the first comparing step.

In the second comparing step, the fourth parameter is compared to the threshold value corresponding thereto (hereinafter, referred to as the second threshold value).

The second threshold value is appropriately set depending on what feature the tumor cell is to be judged. In the case of judging the recurrence risk of the tumor cell, for example, the second threshold value corresponding to the presence or absence of the recurrence with a high possibility can be set when the recurrence risk of the tumor cell whose presence or absence of the recurrence after a predetermined length of time is known is judged in combination with the result of the first comparing step.

The tumor cell collected from the patient is used to prepare a measurement sample used for the measurements of the activation value and the expression level. A method of preparing the sample is not particularly limited as far as the activation values and the expression levels of the CDKs and the growth factor receptor can be measured. A cell lysate can be used as the measurement sample. The cell lysate is a sample obtained in such a manner that a buffer is added to the tumor cell collected from the patient so that the tumor cell is physically and/or chemically ground in the buffer. When the activation value or the expression value of the CDK is measured, a supernatant obtained through centrifugation of the cell lysate is preferably used as the measurement sample. When the protein which belongs to the HER family is used as the growth factor receptor, precipitates obtained through the centrifugation of the cell lysate are preferably used as the measurement sample. The buffer used in this specification may appropriately include a surface active agent or a protease inhibitor.

A method of measuring the activation values of the CDKs or the growth factor receptor is not particularly limited, and any publicly known method can be adopted. As an example can be mentioned a method in which ATP ($\gamma$-[$^{32}$P]-ATP) labeled with $^{32}$P is used. According to the method, the measurement sample, a substrate and ($\gamma$-[$^{32}$P]-ATP are mixed with one another, and $^{32}$P is introduced into the substrate through reactions of the kinases. Next, a label amount of the phosphorylated substrate labeled with $^{32}$P is measured, and the phosphorylated substrate is determined based on a calibration curve generated by means of a calibrator. Then, the activations values of the kinases are calculated based on an amount of the determined phosphorylated substrate. Alternatively, a method recited in No. 2002-335997 of the Japanese Patent Application Laid-Open, in which any radioactive material is not used, can be adopted. According to the method, a sample including one or both of the kinases, a substrate and adenosine 5'-O-(3-thiotriphosphate) (ATP-$\gamma$S) are mixed with one another, and a monothiophosphoric group is introduced into the substrate through the reactions of the kinases. A labeled fluorescent material or a labeled enzyme is bound with a sulfuric atom of the introduced monothiophosphoric group so that the substrate is labeled. Then, the label amount of the labeled monothiophosphoric substrate is measured, and the monothiophosphoric substrate is determined based on the calibration curve generated by means of the calibrator, and the activation values of the kinases are calculated based on the determined monothiophosphoric substrate. In the measurement, a reagent kit comprising a reagent including an anti-CDK antibody, a reagent including the CDK substrate, a reagent including ATP-$\gamma$S and a reagent including a labeled substance which can be bound with the phosphoric substrate can be used. The CDK substrate and ATP-$\gamma$S may be housed in one container.

A method of measuring the expression levels of the CDKs or the growth factor receptor is not particularly limited, and any publicly known method can be used for the measurement. For example, ELISA, western blotting, a method recited in No. 2003-130871 of the Japanese Patent Application Laid-Open, and the like, can be used.

In the measurement sample which is prepared from the tumor cell collected from the patient, the number of the tumor cells included in each measurement sample is different. Accordingly, the measured value of the expression level of the protein, such as the growth factor receptor, is variable depending on if the number of the tumor cells included in the measurement sample is large or small. Therefore, the measured value of the expression level is preferably corrected. For example, an expression level of protein coded by a housekeeping gene (hereinafter, referred to as housekeeping protein) can be used for the correction of the measured value of the expression level. The housekeeping protein is a protein constantly expressed at a certain level in any cell, examples of which include glyceraldehyde-3-phosphate dehydrogenase (GAPDH), actin and the like. More specifically, the measured value of the expression level of the measurement sample can be corrected in such a manner that not only the expression level of the protein of the measurement sample but also the expression level of the housekeeping protein is measured, and the expression level of the protein of the measurement sample is divided by the expression level of the housekeeping protein. In the case where the expression level or the ratio of the activation value and the expression level is used as the first parameter, the expression level or the ratio of the activation value and the expression level is used as the second parameter, and the ratio of the first and second parameters is used as the third parameter, the expression levels of the first and second CDKs are measured. However, the expression level of the housekeeping protein is offset in the calculation, which makes the foregoing correction unnecessary.

In the judging step, the feature of the malignant tumor is determined based on the comparison result of the first comparing step and the comparison result of the second comparing step. For example, when the recurrence risk is predicted as the feature of the malignant tumor, the malignant tumor can be classified into any of three groups respectively having the recurrence risks of different degrees (for example, high, medium and low) based on these results. As specific examples of the method, any of methods 1-5 described below can be used, for example, so that the recurrence risk can be judged.

In the method 1, the result of the comparison of the third parameter to the first threshold value and the result of the comparison of the fourth parameter to the second threshold value are combined so that the recurrence risk is judged. When the respective parameters are below the corresponding threshold values in both of the comparison results, the recurrence risk appears to be low, which is judged as "A1". When the parameter in one of the comparison results is at least the relevant threshold value, and the parameter in the other is below the relevant threshold value, the recurrence risk is judged as "B1" having the recurrence risk higher than that of the tumor cell judged as "A1". When the respective parameters are at least the corresponding threshold values in both of the comparison results, the recurrence risk is judged as "C1" having the recurrence risk higher than that of the tumor cell judged as "B1".

Figure 1:
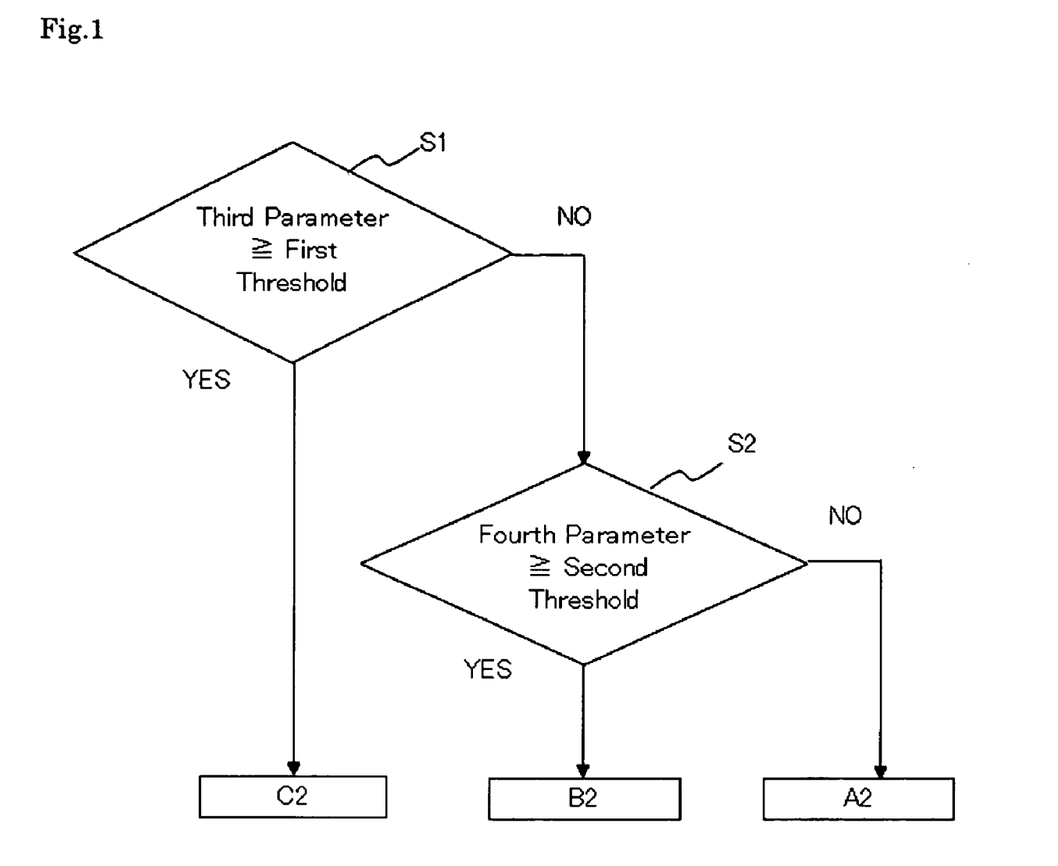
FIG. 1 is a flow chart based on the method 2 of the present embodiment.

The method 2 is a judging method based on a flow chart shown in FIG. 1. In this method, the third parameter is compared to the first threshold value (Step 1), and the recurrence risk is judged as "C2" when the third parameter is at least the threshold value. When the third parameter is below the relevant threshold value, the fourth parameter is compared to the second threshold value (Step 2). Then, the recurrence risk is judged as "B2" having the recurrence risk lower than that of the tumor cell judged as "C2" when the fourth parameter is at least the threshold value. When the fourth parameter is below the relevant threshold value, the recurrence risk is judged as "A2" having the recurrence risk lower than that of the tumor cell judged as "B2". This method places an emphasis on the comparison in which the CDKs are used.

Figure 2:
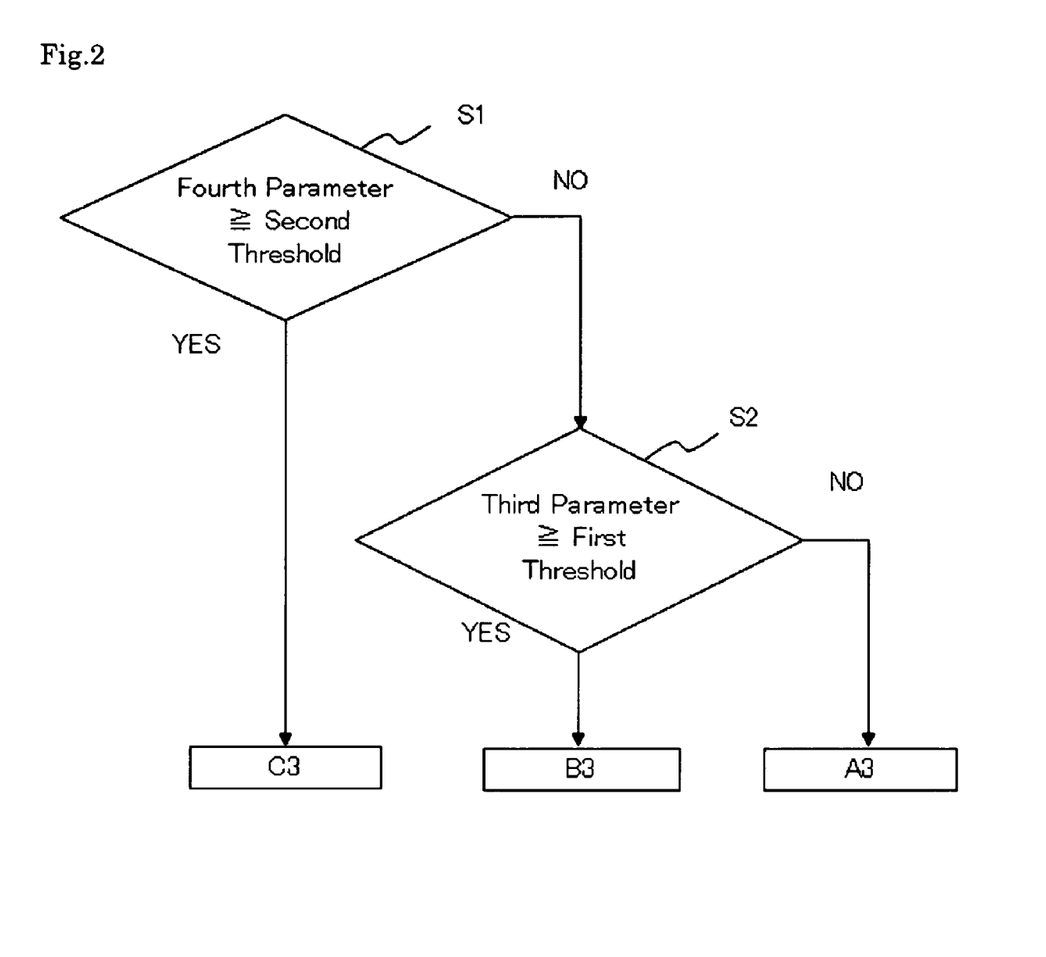
FIG. 2 is a flow chart based on the method 3 of the present embodiment.

The method 3 is a judging method based on a flow chart shown in FIG. 2. In this method, the fourth parameter is compared to the second threshold value (Step 1), and the recurrence risk is judged as "C3" when the fourth parameter is at least the threshold value. When the fourth parameter is below the relevant threshold value, the third parameter is compared to the first threshold value (Step 2). Then, the recurrence risk is judged as "B3" having the recurrence risk lower than that of the tumor cell judged as "C3" when the third parameter is at least the threshold value. When the third parameter is below the relevant threshold value, the recurrence risk is judged as "A3" having the recurrence risk lower than that of the tumor cell judged as "B3". This method places an emphasis on the comparison in which the growth factor is used.

In the method 4, the third parameter is compared to the first threshold value, and the recurrence risk is judged as "A4" when the third parameter is below the threshold value. When the third parameter is at least the relevant threshold value, the fourth parameter is compared to the second threshold value. Then, the recurrence risk is judged as "B4" having the recurrence risk higher than that of the tumor cell judged as "A4" when the fourth parameter is below the threshold value. When the fourth parameter is at least the relevant threshold value, the recurrence risk is judged as "C4" having the recurrence risk higher than that of the tumor cell judged as "B4".

In the method 5, the fourth parameter is compared to the second threshold value, and the recurrence risk is judged as "A5" when the fourth parameter is below the threshold value. When the fourth parameter is at least the relevant threshold value, the third parameter is compared to the first threshold value. Then, the recurrence risk is judged as "B5" having the recurrence risk higher than that of the tumor cell judged as "A5" when the fourth parameter is below the threshold value. When the third parameter is at least the relevant threshold value, the recurrence risk is judged as "C5" having the recurrence risk higher than that of the tumor cell judged as "B5".

Which of the foregoing methods 1-5 is used can be decided in consideration of the type of the malignant cell, the type of the parameter, comparison to clinical data and the like. Any of the methods 1-3 are preferably used in the case of judging the recurrence risk of the malignant tumor.

The CDK is deeply involved in the growth of the cell. Therefore, the proliferation potency of the tumor cell can be accurately grasped when the comparing steps using the CDKs are implemented. As described earlier, the proliferation potency of the cell is a key factor which influences the recurrence risk of the cell.

The growth factor receptor mainly relates to activation of a growth signal path of the cell. Therefore, the recurrence risk of the tumor cell can be predicted when the comparing steps using the growth factor receptor are implemented. However, the growth signal path is subjected to complicated adjustments while transmitting a growth signal, and the risk of recurrence thereby cannot be accurately predicted.

When the judging method according to the present embodiment is used, the foregoing comparison results are combined so that the risk of recurrence can be accurately predicted.

The judgement result of the malignant tumor can be a barometer in selecting a therapeutic method. For example, the method can assist a decision making if an aggressive therapy such as a treatment in which an anticancer agent is used should be conducted or a relatively mild therapy such as a hormone therapy should be conducted to the patient diagnosed of the malignant tumor. Further, a given dose and a type of the anticancer agent to be used can be adjusted depending on the judgement result.

The method of above-stated embodiment is preferably executed as a computer program. Hereinafter, a computer system (FIG. 3) and a flow chart (FIG. 4) will be concretely described with reference to drawings.

Figure 3:
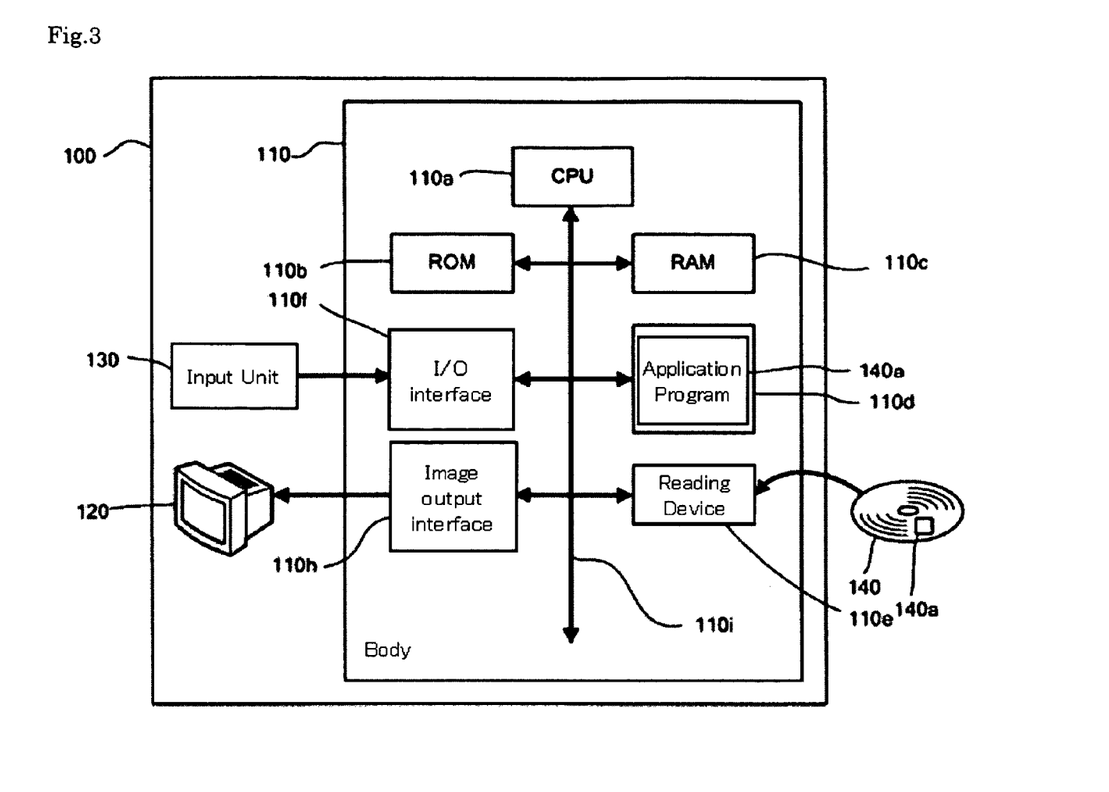
FIG. 3 is a block diagram showing the structure of the computer system 100.

FIG. 3 is a block diagram showing the structure of the computer system 100. This system 100 is mainly configured by body 110, input unit 130 for inputting necessary data to the body 110, and display unit 120. This system 100 can include a portable recording medium 140. A program 140*a* may be recorded in the portable recording medium 140, or may be stored in a memory 110*b*, a memory 110*c* and/or a memory 110*c*. In the body 110, CPU 110*a*, memories 110*b* to 110*d*, Input/Output Interface (I/O interface) 110*f*, image output interface 110*h*, and reading device 110*e* are connected by a bus 110*i*.

Figure 4:
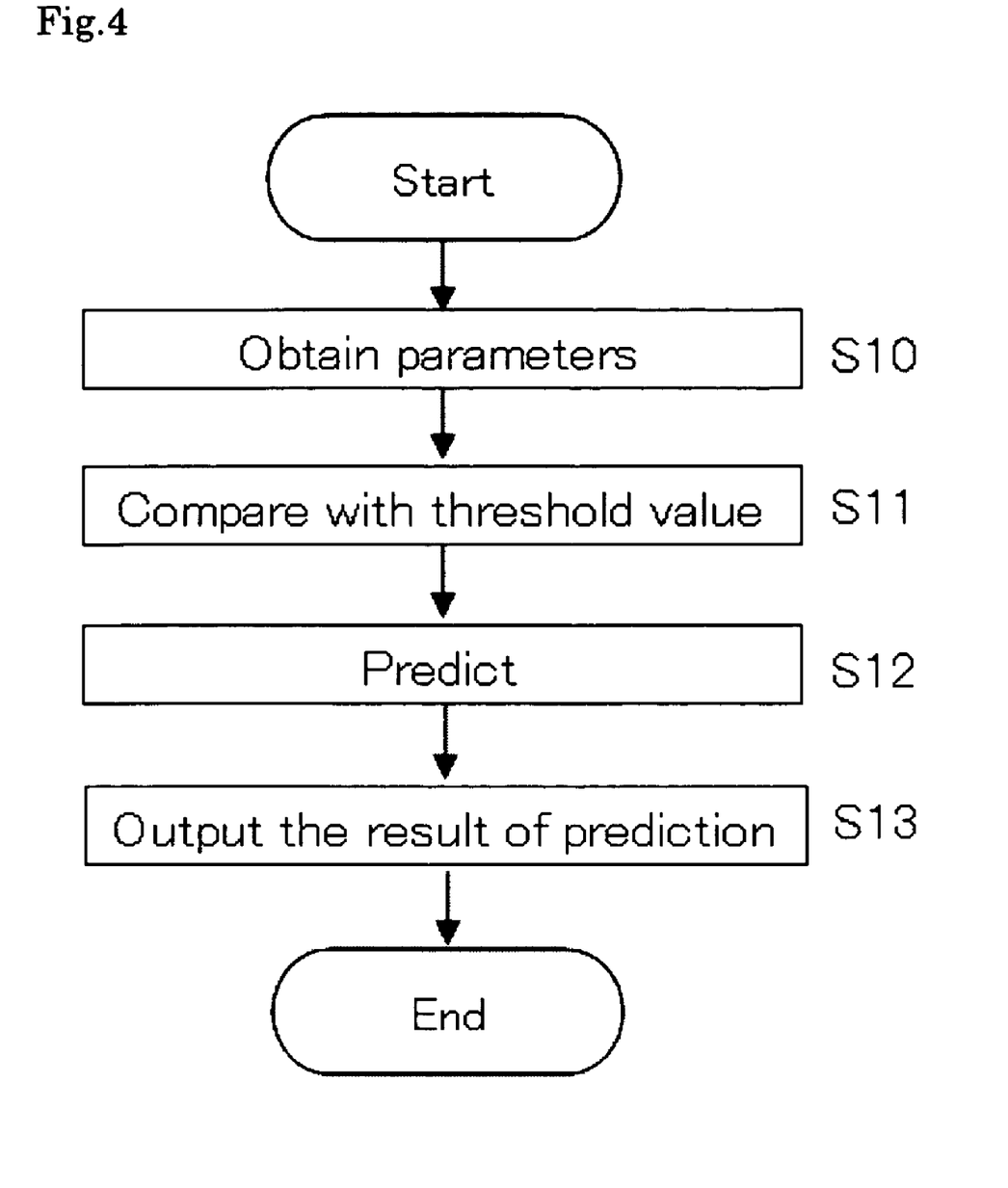
FIG. 4 is a flow chart showing the processing sequence of the computer program for executing above-mentioned Method 1.

FIG. 4 is a flow chart showing the processing sequence of the computer program for executing above-mentioned Method 1. This program is stored in memory 110*d*.

When ratio of CDK2 specific activity and CDK1 specific activity (CDK2 specific activity/CDK1 specific activity: third parameter) and expression level of HER2 (fourth parameter) is input with the input unit 130, CPU 110*a* obtains these parameters through the I/O interface 110*f*, makes RAM 110*c* memorize these parameters (Step S10)

CPU110*a* reads out a threshold corresponding to the third parameter and a threshold corresponding to the fourth parameter which are preliminarily stored in memory 110*d* as data of program. CPU110*a* executes comparison of the third parameter and the threshold, and comparison of the fourth parameter and the threshold (Step S11).

Consequently, CPU110*a* executes a determination based on comparison results (Step S12). Concretely, CPU110*a* determines the sample as "High" risk of recurrence in the case that the third parameter is equal to or more than the threshold and the fourth parameter is equal to or more than the threshold. CPU110*a* determines the sample as "Intermediate" risk of recurrence in the case that the third parameter is equal to or more than the threshold and the fourth parameter is less than the threshold. CPU110*a* determines the sample as "Intermediate" risk of recurrence in the case that the third parameter is less than the threshold and the fourth parameter is equal to or more than the threshold. CPU110*a* determines the sample as "Low" risk of recurrence in the case that the third parameter is less than the threshold and the fourth parameter is less than the threshold.

Further, CPU110*a* stores the determination result in the RAM 110*c*, and output to the display unit 120 through the I/O interface 110*h* (Step S13).

In this embodiment, activity, expression level, and parameter data is input with the input unit 130. It is not limited to this embodiment however, and for instance, the body 110 may automatically obtain the activity, expression level, and parameter data through I/O interface from measuring apparatus(es). Moreover, in this embodiment, although ration of CDK2 specific activity and CDK1 specific activity is input, expression level and activity of CDK2, and expression level and activity of CDK1 may be input. In this case, CPU110*a* can calculate ration of CDK2 specific activity and CDK1 specific activity, and compare the ration to the threshold.

Working Example 1

1) Preparation of Measurement Sample

Measurement samples i-xii were prepared from 12 specimens of tumor cell blocks (13-92 mg) extirpated from 12 breast cancer patients (patients i-xii) in the stage IIB as follows.

First, a buffer A (including 0.1 w/v % of Nonidet P-40 (Calbiochem Inc.), 50 mM of tris-hydrochloric acid (pH 7.4), 5 mM of EDTA, 50 mM of sodium fluoride, 1 mM of sodium orthovanadate, 100 μl/ml of protease inhibitor cocktail (SIGMA CORPORATION)), and the tumor cell block were housed in a tube so that the tumor cell block in the buffer was approximately 150 mg/ml.

The tumor cell block was homogenized in the buffer A by means of an electric homogenizer so that the tumor cells were ground, and a cell lysate was thereby prepared. Next, the cell lysate was centrifuged at 4° C. and 15,000 rpm for five minutes, and precipitates were used as the HER2 measurement sample, while a supernatant was used as the CDK measurement sample.

2) Measurement of Expression Levels of HER2 nad GAPDH

A buffer B (including 1% of TritonX-100, 0.1% of sodium deoxycholic acid, 0.1% of SDS, 50 mM of tris-hydrochloric acid (pH 8.0), 150 mM of NaCl, 0.5 mM of EDTA, and 0.2% of protease inhibitor cocktail (SIGMA CORPORATION)) was added to the HER2 measurement sample, and the resulting substance was centrifuged at 15,000 rpm for five minutes. After the centrifugation, the supernatant was obtained, and a SDS loading buffer (including 200 mM of tris-hydrochloric acid (pH 6.8), 40% of glycerol, 8% of SDS, 10% of 2-melcaptoethanol) in the amount of ⅓ of the supernatant was added to the supernatant. Then, the resulting substance was heated at 100° C. for five minutes.

10 µl of the HER2 measurement sample after the heating process was used to perform SDS-PAGE, and the gel was dipped in a transfer buffer (including 192 mM of glycine, 25 mM of tris and 20% of methanol) at room temperature for five minutes to be thereby equalized.

Protein in the gel was transferred onto the Immobilon FL membrane (Millipore Corporation) at 100V and 4° C. for an hour by means of the Mini Trans-Blot cell transfer system (Bio-Rad Laboratories, Inc.).

The membrane was blocked with a blocking reagent A (including 4% of BSA, 25 mM of tris-hydrochloric acid (pH 7.4), 150 mM of NaCl and 0.02% of Tween 20) at 37° C. for an hour, and washed with a washing solution A (including 25 mM of tris-hydrochloric acid (pH 7.4), 150 mM of NaCl, and 0.02% of Tween 20).

After the washing process, 5 ml of a rabbit anti-HER2 antibody (first antibody: Upstate Group, Inc.) solution was blotted in the membrane so that the HER2 of the membrane and the first antibody were reacted with each other.

The membrane was washed with 20 ml of the washing solution A, and thereafter, 5 ml of a biotin-labeled goat anti-rabbit IgG-B (second antibody: Santa Cruz Biotechnology Inc.) solution was blotted in the membrane so that the first and second antibodies in the membrane were reacted with each other.

The membrane was washed with 20 ml of the washing solution A, and thereafter, 5 ml of an Alexa fluor 488 conjugated streptabidin (Molecular Probes Inc.) solution as fluorochrome was blotted in the membrane so that the second antibody and the fluorochrome were reacted with each other.

The membrane was washed with 20 ml of the washing solution A, and thereafter, an amount of HER2 adsorbed to the membrane was analyzed and measured by the Molecular Imager FX (Bio-Rad Laboratories, Inc.) which was a fluorescence image analyzer.

The expression level of the GAPDH was measured in an experimental procedure similar that of the measurement of the expression level of the HER2 except for the use of the supernatant of the cell lysate as the measurement sample and the use of not the rabbit anti-HER2 antibody but a rabbit anti-GAPDH antibody as the first antibody.

The GAPDH expression level was used to correct the measured value of the HER2 expression level. A value shown below as the HER2 expression level is a value after the correction using the GAPDH expression level (value of HER2 expression level/GAPDH expression level).

Figure 5:
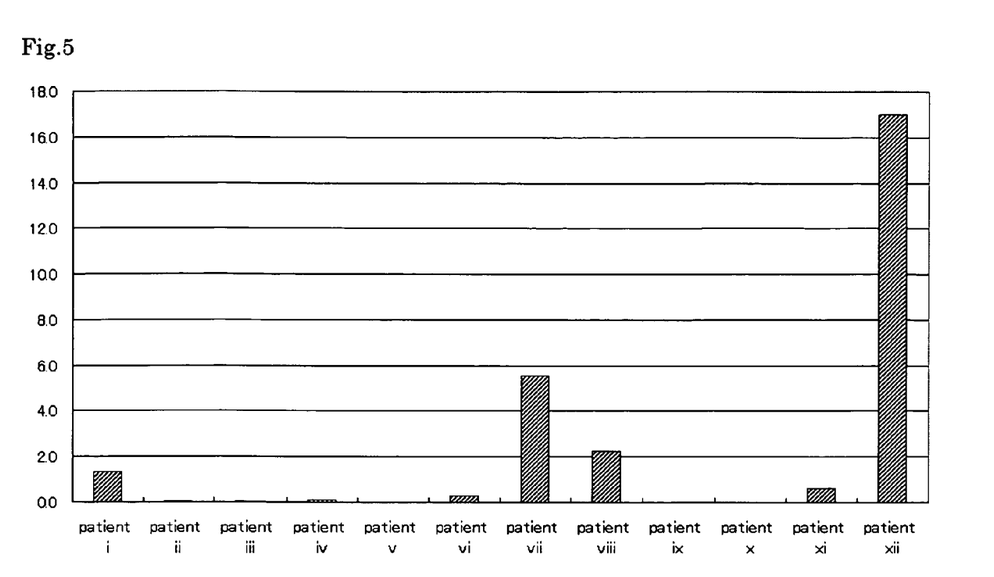
FIG. 5 is a graph of the measurement result of the HER2 expression level.

The measurement result of the HER2 expression level is shown in the following tables 1 and graph of FIG. 5.

3) Measurement of Expression Levels of CDK1 and CDK2

50 µl each of the CDK measurement samples was housed in each well of a blotter set in a PVDF membrane (Millipore Corporation). Then, the CDK measurement sample was suctioned from a bottom surface of the well, which is a rear surface of the membrane, at a negative pressure of approximately 250 mmHg for approximately 30 seconds so that protein in the CDK measurement sample was adsorbed to the membrane.

100 µl of a washing solution B (including 25 mM of tris-hydrochloric acid (pH 7.4) and 150 mM of NaCl) was housed in each well and suctioned at the negative pressure of 500 mmHg for 15 seconds so that the membrane was washed.

After the washing process, 40 µl of a blocking reagent B (4% of BSA, 25 mM of tris-hydrochloric acid (pH 7.4) and 150 mM of NaCl) was housed in each well and left in a stationary state for 15 minutes, and suctioned at the negative pressure of 500 mmHg for 15 seconds so that the membrane was blocked.

After the blocking process, 40 µl of a rabbit anti-CDK1 antibody (first antibody: Santa Cruz Biotechnology Inc.) which is specifically bound with the CDK1 was housed in each well and left in the stationary state at room temperature for approximately 30 minutes so that the CDK1 in the membrane and the first antibody were reacted with each other. Then, the suction was applied thereto from the bottom surface of the well at the negative pressure of 500 mmHg for approximately 15 seconds.

100 µl of the washing solution B was housed in each well and suctioned at the negative pressure of 500 mmHg for 15 seconds so that the membrane was washed.

40 µl of a biotinylated anti-rabbit CDK1 antibody (second antibody: Santa Cruz Biotechnology Inc.) solution was housed in each well and left in the stationary state at room temperature for approximately 30 minutes so that the first antibody was reacted with second antibody in the membrane. Thereafter, the suction was applied thereto from the bottom surface of the well at the negative pressure of 500 mmHg for approximately 15 seconds.

100 µl of the washing solution B was housed in each well and suctioned at the negative pressure of 500 mmHg for 15 seconds so that the membrane was washed.

50 µl of a labeled solution including FITC-labeled streptavidin was housed in each well and left in the stationary state at room temperature for approximately 30 minutes so that the second antibody in the membrane was FITC-labeled. Thereafter, the suction was applied thereto from the bottom surface of the well at the negative pressure of 500 mmHg for approximately 15 minutes.

50 µl of the washing solution B was housed in each well and suctioned at the negative pressure of 500 mmHg for 15 seconds, which was repeated five times so that the membrane was washed.

The membrane was removed from the blotter, washed with 20% methanol for approximately five minutes and dried at room temperature for approximately 20 minutes. Thereafter, fluorescence intensity of the protein adsorbed to the membrane was analyzed and measured by the Molecular Imager FX (Bio-Rad Laboratories Inc.) which was the fluorescence image analyzer. The measurement value was calculated based on the calibration curve.

The calibration curve was generated in such a manner that 50 µl of a solution obtained by dissolving recombined CDK1s of five different concentrations in a washing solution B including 0.005% of Nonidet P-40 and 50 µg/ml of BSA was injected into each well processed in a manner similar to the foregoing description and FITC-labeled in an experimental procedure similar to the foregoing description and fluorescence intensity thereof was measured so that a relationship between the fluorescence intensity and the expression level of the CDK1 was expressed.

The expression level of the CDK2 was measured in an experimental procedure similar to the measurement of the expression level of the CDK1 described earlier except for the use of not the rabbit anti-CDK1 antibody but a rabbit anti-CDK2 antibody as the first antibody.

4) Measurement of Activities of CDK1 and CDK2

500 μl of the buffer A was housed in an Eppendorf tube of 1.5 ml, and the CDK measurement sample was added thereto. The CDK measurement sample was prepared so that a total protein amount in the mixed solution housed in the tube was 100 μg and then added.

2 μg of the anti-CDK1 antibody (Santa Cruz Biotechnologies Inc.) and 20 μl of Sepharose beads (Bio-Rad Laboratories, Inc.) coated with protein A was added to the foregoing substance and left in the stationary state at 4° C. for an hour so that the CDK1 and the anti-CDK1 antibody were reacted with each other.

After the reaction, the beads were washed three times with a beads washing buffer (including 0.1 w/v % of Nonidet P-40 and 50 mM of tris-hydrochloric acid (pH 7.0)) and suspended in 15 μl of the lysis buffer A again. As a result, a sample including Sepharose beads with which the CDK1 is bound via the anti-CDK1 antibody could be obtained.

10 μg of a substrate solution of the CDK1 (including 10 μg of histone H1 (Upstate Biotechnology Inc.), 5 mM of ATP-γS (SIGMA CORPORATION), and 20 mM of tris-hydrochloric acid (pH 7.4) and 0.1% of TritonX-100) was added to the sample. The substrate solution was prepared so that a total amount of the mixed solution housed in the tube was 50 μl and then added. The resulting substance was shaken at 37° C. for 10 minutes to induce the kinase reaction so that the monothiophosphoric acid group was introduced into the histone H1.

After the kinase reaction, the foregoing substance was centrifuged at 2,000 rpm for 20 seconds so that the beads were precipitated. As a result, a supernatant in the amount of 18 μl was obtained.

15 μl of a binding buffer (including 150 mM of tris-hydrochloric acid (pH 9.2) and 5 mM of EDTA) and 10 mM of an iodoacetylbiotin solution (including 100 mM of tris-hydrochloric acid (pH 7.5) and 1 mM of EDTA) were added to the supernatant and left in the stationary state at room temperature and in a dark place for 90 minutes so that the iodoacetylbiotin was bound with a sulfuric atom of the substrate (monothiophosphoric acid substrate) into which the monothiophosphoric acid group was introduced.

The reaction between the iodoacetylbiotin and the monothiophosphoric acid group was halted by the addition of 2-melcaptoethanol.

A sample including 0.4 μg of the monothiophosphoric acid substrate with which the iodoacetylbiotin was bound was blotted onto the PVDF membrane by means of the slot blotter.

The PVDF membrane was blocked with a solution including 1 w/v % of BSA, and streptavidin-FITC (Vector Laboratories Inc.) was added thereto, which was reacted at 37° C. for an hour.

After the reaction, the PVDF membrane was washed with 50 mM of the washing solution B three times.

After the washing, a fluorescence analysis was conducted to the PVDF membrane by means of the Molecular Imager FX (Bio-Rad Laboratories, Inc.) which was the fluorescence image analyzer. The activation value was calculated based on the calibration curve.

The calibration curve was generated in such a manner that a solution including proteins having two different concentrations (biotin-labeled immunoglobulin) were blotted onto the PVDF membrane, FITC-labeled in a method similar to the foregoing description, and the fluorescence intensities of the proteins were measured with the fluorescence image analyzer. Therefore, an activation IU (unit) of the measured CDK1 denotes a value indicating fluorescence intensity equal to the fluorescence amount when the protein is 1 ng.

The activation value of the CDK2 was measured in a manner similar to the measurement of the activation value of the CDK1 except for the use of the anti-CDK2 antibody (Santa Cruz Biotechnology Inc.).

5) Calculation of CDK Specific Activity

The CDK specific activity (mU/ng) was calculated from the CDK activation value and the CDK expression value calculated above in the following formula.

CDK specific activity=CDK activation value/CDK expression level

Figure 6:
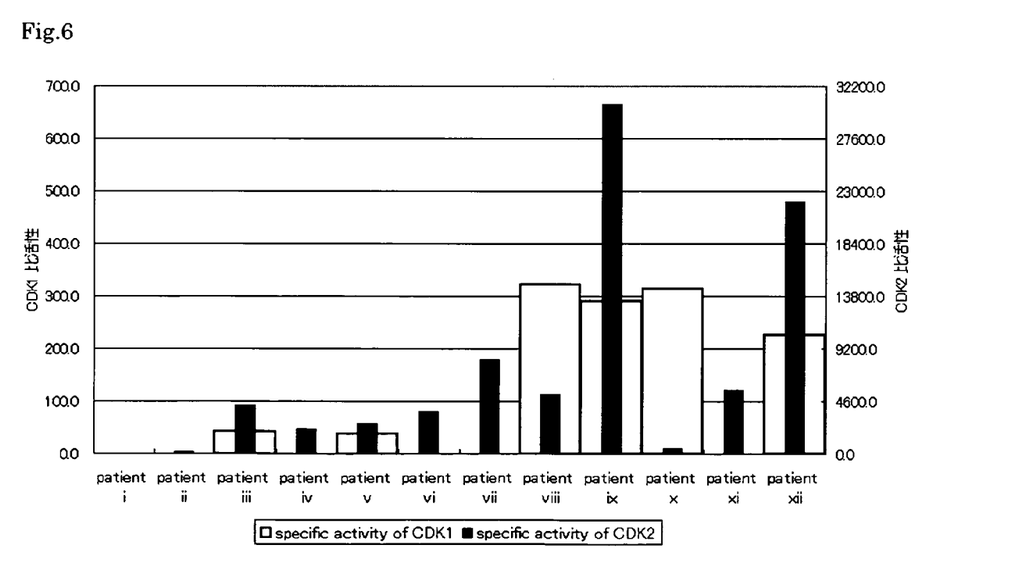
FIG. 6 is a graph of the measurement results of the specific activities of the CDK1 and the CDK2.

The measurement results of the specific activities of the CDK1 and the CDK2 are shown in the following tables 1 and graph of FIG. 6.

6) Threshold Setting and Recurrence Risk Judgement

A threshold value corresponding to a ratio of the specific activities of the CDK1 and the CDK2 (CDK2 specific activity/CDK1 specific activity; hereinafter, referred to as ratio of specific activities) was set, and a threshold value corresponding to the expression level of the HER2 was set. Then, a result obtained from comparing the ratio of the specific activities to the relevant threshold value and a result obtained from comparing the expression level of the HER2 to the relevant threshold value were combined so that the feature of the tumor cell was judged.

The threshold value for the ratio of the specific activities was set to 46. The value is capable of separating 129 specimens as 65:64 when the ratios of the specific activities of the 129 tumor cell specimens collected from 129 breast cancer patients are calculated and listed from the smaller values of the ratio of the specific activities.

The value of the ratio of the specific activities being at least 46 was judged as "High", while the value below 46 was judged as "Low". In the case of the specific activity of the CDK1 being below 20 and the specific activity of the CDK2 being below 500, the judgement was "Low" irrespective of the ratio of the specific activities. In the case of the specific activity of the CDK2 being at least 10,000, the judgement was "High" irrespective of the ratio of the specific activities.

The threshold value for the expression level of the HER2 was set to 0.7. The value was set in terms of the presence or absence of the recurrence in the patients i-xii and the comparison results of the ratio of the specific activities and the corresponding threshold value. The judgement was "High" when the expression level of HER2 is at least 0.7, while "Low" when below 0.7.

These comparison results were used so that the recurrence risk was judged based on the following judgement conditions.

The judgement was "recurrence risk is "LOW" when the comparison result between the ratio of the specific activities and the threshold value is "Low", and the comparison result between the HER 2 expression level and the threshold value is "Low".

The judgement was "recurrence risk is "INTERMEDIATE" when the comparison result between the ratio of the specific activities and the threshold value is "High", and the comparison result between the HER 2 expression level and the threshold value is "Low".

The judgement was "recurrence risk is INTERMEDIATE" when the comparison result between the ratio of the specific activities and the threshold value is "Low", and the comparison result between the HER 2 expression level and the threshold value is "High".

The judgement was "recurrence risk is HIGH" when the comparison result between the ratio of the specific activities and the threshold value is "High", and the comparison result between the HER 2 expression level and the threshold value is "High".

In the tumor cell judged as "recurrence risk is LOW" in the recurrence risk judgement, the proliferation potency, survival potency and migratory aptitude of the cell appear to be low, and the recurrence risk is judged as low. The tumor cell judged as "recurrence risk is INTERMEDIATE" is judged as having the recurrence risk higher than that of the tumor cell judged as "recurrence risk is LOW". The tumor cell judged as "recurrence risk is HIGH" is judged as having the recurrence risk higher than that the tumor cell judged as "recurrence risk is INTERMEDIATE".

The presence or absence of the recurrence (in the table, "−" denotes "no recurrence", and "+" denotes "recurrence is detected"), measurement results of the foregoing molecules, comparison results with respect to the threshold values and judgement result of the recurrence risk in relation to the patients i-xii are collectively shown in the following table 1. "The presence or absence of the recurrence" indicates that the follow research is conducted to the respective patients i-xii after the tumor cell blocks are extirpated from them to confirm whether or not the recurrence is diagnosed in five years from the extirpation.

TABLE 1

|  | recurrence | specific activity of CDK1 | specific activity of CDK2 | comparison of ratio with threshold | expression level of HER2 | comparison of expression level with threshold | risk of recurrence |
|---|---|---|---|---|---|---|---|
| patient i | − | 0.0 | 26.0 | Low | 1.344 | High | INTERMEDIATE |
| patient ii | − | 0.0 | 228.7 | Low | 0.055 | Low | LOW |
| patient iii | − | 41.6 | 4219.4 | High | 0.048 | Low | INTERMEDIATE |
| patient iv | − | 0.0 | 2167.3 | High | 0.108 | Low | INTERMEDIATE |
| patient v | − | 38.4 | 2632.3 | High | 0.004 | Low | INTERMEDIATE |
| patient vi | − | 0.0 | 3666.9 | High | 0.303 | Low | INTERMEDIATE |
| patient vii | + | 0.0 | 8275.4 | High | 5.565 | High | HIGH |
| patient viii | + | 322.0 | 5392.6 | Low | 2.257 | High | INTERMEDIATE |
| patient ix | + | 290.5 | 30643.5 | High | 0.000 | Low | INTERMEDIATE |
| patient x | − | 313.2 | 482.3 | Low | 0.022 | Low | LOW |
| patient xi | − | 0.0 | 5621.0 | High | 0.633 | Low | INTERMEDIATE |
| patient xii | + | 226.2 | 22050.0 | High | 16.994 | High | HIGH |

There was no tumor recurrence in the patients ii and x whose recurrence risks were judged as LOW in five years after the operations (recurrence ratio 0%). The tumor recurrence was detected in two of the eight patients i, iii, iv, v, vi, viii, ix and xi whose recurrence risks were judged as INTERMEDIATE in five years after the operations (recurrence ratio 25%). The patients vii and xii whose recurrence risks were judged as HIGH both had the tumor recurrence in five years after the operations (recurrence ratio 100%).

As described thus far, when the comparison result between the ratio of the CDK specific activities and the threshold value and the comparison result between the HER2 expression level and the threshold value are combined, the patients can be classified into the three groups respectively having the recurrence risks at different degrees, and the presence or absence of the recurrence can be thereby predicted. Further, the prediction result can be used as a key factor in deciding the therapeutic policy for the malignant tumor patient.

What is claimed is:

1. A computer-implemented method for judging a risk of recurrence of breast cancer, comprising steps of:
    obtaining a ratio of a specific activity for cyclin dependent kinase 2 (CDK2) and a specific activity for CDK1, and an expression level of HER2 contained in a tumor cell of the malignant tumor, wherein the specific activity for the CDK2 is the ratio of an activation value of the CDK2 and an expression level of the CDK2 contained in the tumor cell, and the specific activity for the CDK1 is the ratio of a activation value of the CDK1 and an expression level of the CDK1 contained in the tumor cell;
    first comparing a first threshold value stored in a memory with the ratio of the CDK2 specific activity and the CDK1 specific activity;
    second comparing a second threshold value stored in the memory with the expression level of HER2;
    judging a risk level on the basis of the first comparison result, the second comparison result and risk information which represents relationship of risk levels, a ratio of CDK2 specific activity and CDK1 specific activity, and a expression level of HER2, and is stored in the memory, and
    displaying the judged risk level on a display, wherein every method step is executed by a sufficiently programmed computer.

2. The method according to claim 1, wherein the risk levels comprise high risk, intermediate risk and low risk.

3. The method according to claim 2, wherein the judging step is performed by judging the risk of recurrence is high risk when the ratio of the CDK2 specific activity and the CDK1 specific activity is higher than the first threshold value and the expression level of HER2 is higher than the second threshold value.

4. The method according to claim 2, wherein the judging step is performed by judging the risk of recurrence is low risk when the ratio of the CDK2 specific activity and the CDK1 specific activity is not higher than the first threshold value and the expression level of HER2 is not higher than the second threshold value.

5. The method according to claim 2, wherein the judging step is preformed by judging the risk of recurrence is intermediate risk when the ratio of the CDK2 specific activity and the CDK1 specific activity is higher than the first threshold value and the expression level of HER2 is not higher than the second threshold value.

6. The method according to claim 2, wherein the judging step is preformed by judging the risk of recurrence is intermediate risk when the ratio of the CDK2 specific activity and the CDK1 specific activity is not higher than the first threshold value and the expression level of HER2 is higher than the second threshold value.

7. The method according to claim 1, wherein breast cancer belongs to Stage TIE in stage classification.

8. A computer-recordable medium having stored thereon instructions to perform a process for judging the risk of recurrence of breast cancer obtaining a ratio of a specific activity for cyclin dependent kinase 2 (CDK2) and a specific activity for CDK1, and an expression level of HER2 contained in a tumor cell of the malignant tumor, wherein the specific activity for the CDK2 is the ratio of an activation value of the CDK2 and an expression level of the CDK2 contained in the tumor cell, and the specific activity for the CDK1 is the ratio of an activation value of the CDK1 and an expression level of the CDK1 contained in the tumor cell, first comparing a first threshold value stored in a memory with the ratio of the CDK2 specific activity and the CDK1 specific activity, second comparing a second threshold value stored in the memory with the expression level of HER2, judging the risk on the basis of the first comparison result, the second comparison result and risk information which represents relationship of risk groups, a ratio of the CDK2 specific activity and the CDK1 specific activity, and a expression level of HER2, and is stored in the memory, and displaying the judged risk group on a display.

* * * * *